US006842656B1

United States Patent
Burkhardt et al.

(10) Patent No.: US 6,842,656 B1
(45) Date of Patent: Jan. 11, 2005

(54) METHOD AND DEVICE FOR THE PROCESS-OPTIMIZING REGULATION OF PARAMETERS IN A PRODUCTION PROCESS

(75) Inventors: Steffen Burkhardt, Chemnitz (DE); Karl Schäfer, Aachen (DE)

(73) Assignee: Parsytec Computer GmbH, Aachen (DE)

( * ) Notice: Subject to any disclaimer, the term of this patent is extended or adjusted under 35 U.S.C. 154(b) by 85 days.

(21) Appl. No.: 10/030,238

(22) PCT Filed: Jun. 2, 2000

(86) PCT No.: PCT/EP00/05085

§ 371 (c)(1),
(2), (4) Date: Mar. 12, 2002

(87) PCT Pub. No.: WO01/02840

PCT Pub. Date: Jan. 11, 2001

(30) Foreign Application Priority Data

Jun. 30, 1999 (DE) .......................... 199 30 173

(51) Int. Cl.⁷ .............................. G06F 19/00
(52) U.S. Cl. .................. 700/110; 700/109; 700/148; 700/150
(58) Field of Search ................. 700/109, 110, 700/148–156

(56) References Cited

U.S. PATENT DOCUMENTS

| | | | | |
|---|---|---|---|---|
| 4,131,490 A | * | 12/1978 | Oishi et al. ................ | 148/196 |
| 4,752,897 A | | 6/1988 | Zoeller et al. | |
| 5,710,700 A | * | 1/1998 | Kurtzberg et al. ........... | 700/29 |
| 5,745,365 A | | 4/1998 | Parker | |
| 5,854,749 A | * | 12/1998 | Kellams et al. ............ | 700/146 |
| 5,896,294 A | * | 4/1999 | Chow et al. ............... | 700/121 |
| 5,899,959 A | | 5/1999 | Shields | |
| 5,991,699 A | * | 11/1999 | Kulkarni et al. ............. | 702/83 |
| 6,044,895 A | * | 4/2000 | Kuttner et al. ............. | 165/155.4 |
| 6,232,617 B1 | * | 5/2001 | Vanhee ................... | 250/559.45 |
| 6,292,260 B1 | * | 9/2001 | Lin et al. ................. | 356/237.4 |
| 6,327,374 B1 | * | 12/2001 | Piironen et al. ............. | 382/108 |
| 6,415,044 B1 | * | 7/2002 | Simpson et al. ............. | 382/108 |
| 6,430,461 B1 | * | 8/2002 | Andorfer et al. ........... | 700/148 |
| 6,546,310 B1 | * | 4/2003 | Doll et al. ................ | 700/150 |
| 6,594,590 B2 | * | 7/2003 | Woods et al. .............. | 702/35 |

FOREIGN PATENT DOCUMENTS

| | | |
|---|---|---|
| DE | 22 00 293 C2 | 8/1972 |
| DE | 43 43 058 A1 | 6/1995 |
| DE | 195 18 804 A1 | 12/1995 |
| DE | 196 32 269 A1 | 2/1997 |
| DE | 197 20 307 A1 | 11/1998 |
| EP | 0 176 661 A2 | 4/1986 |

OTHER PUBLICATIONS

Reinhard Rinn et al.: "Parsytec HTS–2, Defect Detction and Classification through Software vs. Dedicated Hardware", Part of the IS&T/SPIE Conference on Real–Time Imaging IV, San Jose, California, Jan. 1999, SPIE, vol. 3645, pp. 110–121.

* cited by examiner

*Primary Examiner*—Leo Picard
*Assistant Examiner*—Elliot L. Frank
(74) *Attorney, Agent, or Firm*—Laurence A. Greenberg; Werner H. Stemer; Gregory L. Mayback

(57) ABSTRACT

A surface of a long flat product is observed in a production process by way of a surface inspection system. The entire surface is plotted, on the basis of the observation data, as a surface map with established surface characteristics in the, form of surface data and the surface characteristics are classified according to the different types and/or sizes and/or frequency and registered in the surface map according to their position. Production data and product data are jointly fed to a data processing unit in which they are analyzed to determine correlations between them. Rules dealing with the dependence of product data upon given production data are determined so that process parameters can be regulated in line with the rules thus determined to obtain a desired quality. Interrelationships can be recognized between process parameters and the emergence of surface errors, for instance in continuous casting and rolling facilities for steel sheets.

14 Claims, 1 Drawing Sheet

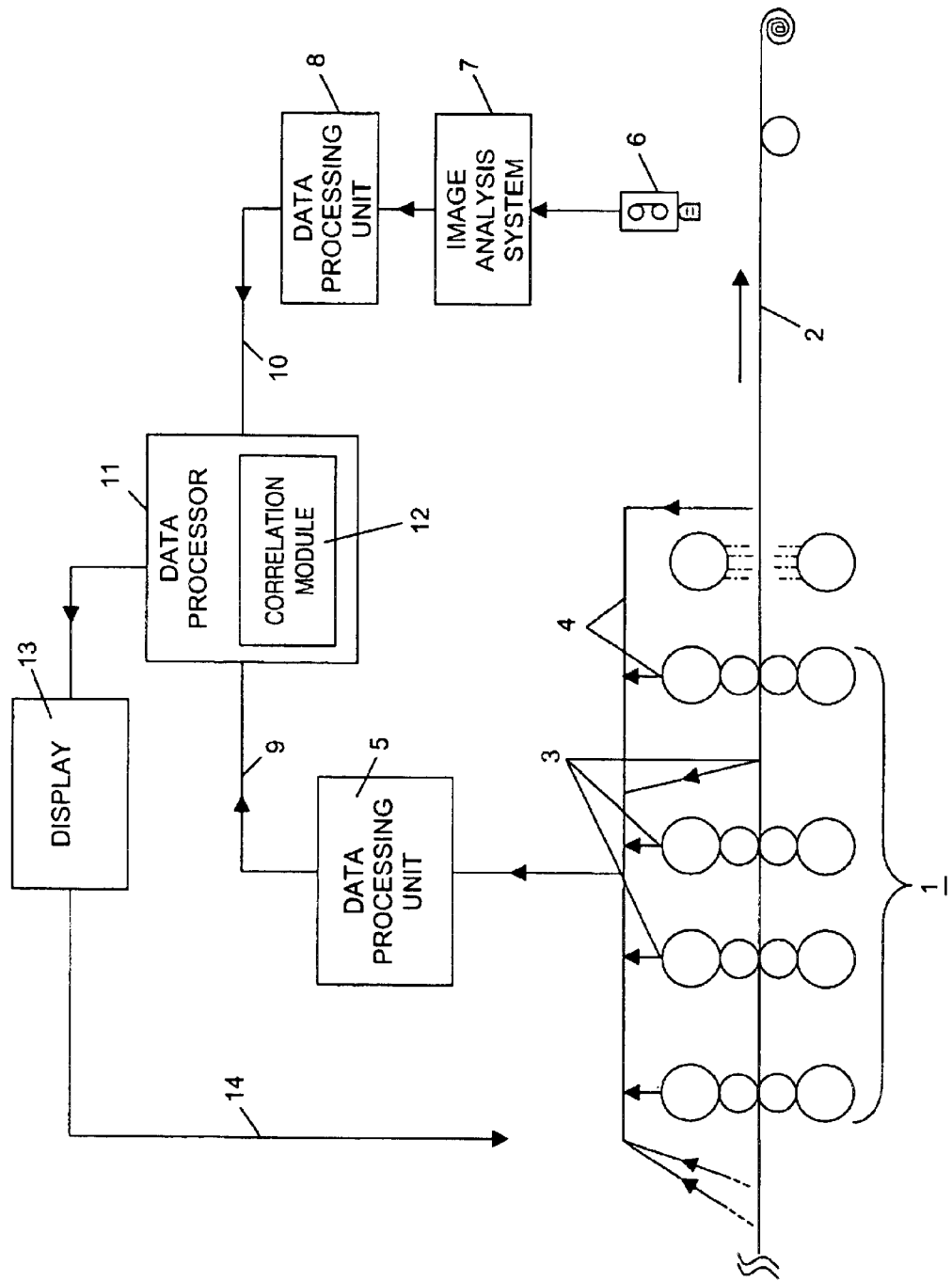

METHOD AND DEVICE FOR THE PROCESS-OPTIMIZING REGULATION OF PARAMETERS IN A PRODUCTION PROCESS

BACKGROUND OF THE INVENTION

Field of the Invention

The present invention relates to a method and a device for setting process parameters of a production process for an elongate sheet-like product to achieve a predeterminable product quality.

In production processes, in particular continuous processes for the production of elongate sheet-like products, for example rolled steel, it is necessary to set a large number of process parameters to suitable values in order to achieve a smooth production procedure and good quality of the product.

If for example the production of rolled steel is considered, taken by way of example as a particular area of application, of the present invention, it becomes evident that numerous production parameters have an influence on the final product. This begins with the metallurgical composition of the melt, with its treatment in the melting pan, continues with the parameters during the casting operation and the thermal profiles prevailing there and then relates in particular to the hot-rolling mill with many parameters such as rolling pressure, temperature of the strip etc. A large number of measured values in all stages of production serve for controlling the production parameters, it often needing decades of experience on the part of the operating personnel to keep a production process stable and achieve a desired quality of product in each case. In particular in the case of newly designed and newly constructed installations, it is often difficult to find out the correct production parameters for achieving a specific product quality.

Of course, it has always been possible to measure simple product characteristics such as width and thickness of the strip during the production process and to control them by changing production parameters decisive for these characteristics.

For sheet-like products, however, not only the dimensions and the composition of the material are significant but most particularly also the condition of the surface. While in the past it was not possible in practice, with a strip running at high speed, to inspect the surface continuously, detect defects and classify them, there have for some time been surface inspection systems based on cameras with downstream networked image analysis systems which make surface inspection possible even while a strip is running.

In particular, such surface inspection systems have been used in the past for quality control, i.e. these systems produced a kind of map of the surface of a steel strip, onto which observed defects could be entered with their position and also be classified according to type and frequency and, for example, periodicity. In this way, it was possible for finished rolls of sheet to be provided with quality certificates, providing information on the location, type and/or frequency of defects. Such a surface inspection system is described for example in DE 197 20 307 A1 or DE 197 30 622.

The surface maps were able to provide valuable information during subsequent inspection as to locations in the production process at which specific defects were caused, but this could neither be automated nor systemized.

SUMMARY OF THE INVENTION

The object of the present invention is to be able to investigate the data obtained by means of a surface inspection system systematically for possible correlations with process data, with the aim of finding dependencies of the product quality on specific process parameters and thus be able to control a process more quickly and reliably to achieve a predetermined quality. In particular, it is intended that the correlation can also be used online in production processes, in particular in the case of cast-rolling installations for, steel sheets in the hot-rolling process. Apart from finding interrelationships based on theoretical principles between production parameters and product quality, it is also intended in particular to achieve immediate feedback to the production process for controlling the parameters responsible for specific deviations in quality.

A method as claimed in claim 1 and a device as claimed in claim 8 serve to achieve this object. Advantageous refinements are specified in the respectively dependent claims.

To illustrate the complexity of the problem to be solved, it should firstly be pointed out that the number of measured values in the exemplary embodiment described here may reach approximately 1,000,000 values per minute. The data of a surface inspection system also reach approximately this order of magnitude. In this case, the parameters may be of various kinds for the characterization of continuous or discrete variables or purely Boolean variables, which can only assume two values.

According to the invention, numerous process parameters of the production process are recorded as a function of time in the form of process data, and the process data are processed in at least a first data processing unit and output as production data. At the same time, the surface of the product is observed by means of a surface inspection system within or at the end of the production process, the observation data being used in at least a second data processing unit to record the surface as a kind of surface map with established surface features in the form of surface data and to classify the surface features according to various types and/or according to size and/or according to frequency and enter them in the surface map according to their position. The various classes and positions of surface features are output as product data. The production data and the product data are subsequently fed together to at least a third data processing unit and investigated there for correlations existing between them, with rules as to how the product data depend on specific production data being established. After that, the process parameters can be set in accordance with the established rules and their interpretation in the form of suitable control signals to achieve a desired quality. The preselection and evaluation both of the production data and of the product data in data processing units operating in parallel produce selected production and product data, already presorted and assessed according to certain aspects, for a correlation investigation. Therefore, installed in the third data processing unit is a correlation module, which investigates the data fed to it for significant correlations. Various correlation principles come into consideration for such a correlation module. Examples of this are neural methods and statistical methods. Preferred in the case of the present invention is a program which is based on the fact that the data to be correlated are presented in a data space as far as possible in such a way that the entropy is minimized. This produces accumulations of data at specific locations in the data space, which indicate correlations and can be formulated in the form of theoretical principles or dependencies.

Such a correlator initially produces as its result empirical and theoretically unexplained relationships between production parameters and product data, from which desired-value settings for the production parameters can be derived to achieve specific product qualities and can be set during production.

The invention makes it possible for the first time to correlate complex surface data of the final product with production parameters virtually online and consequently allows the finding of theoretical principles and relationships which previously could not be detected on account of their complexity. It is only the preparation of surface data obtained by the detection and classification of surface defects that allows the mass of data during the observation of the surface by cameras to be brought to a scale which permits sufficiently quick investigation for correlations with production parameters.

With the great mass of data, an important factor is the function of the first data processing unit 5, and of the second data processing unit 8. A preselection of data, known as aggregation of the data, can take place there on the basis of criteria predetermined by the user, to exclude data detected as unimportant for the respective task or generally. On the other hand, certain primary data detected as important can also be passed on quickly there, without any processing, in order that it is available in the third data processing unit for the analysis of correlations. In particular, after finding certain correlations it is possible for the specific data which correlate with other data to be passed on.

During the operation of the complete device, the analysis of increasing amounts of data and finding of various correlations produce a certain number of dependencies, which on the one hand can be visually presented, printed out or stored as rules, but on the other hand can also be fed back automatically for controlling the production arrangement to maintain a specific quality.

BRIEF DESCRIPTION OF THE DRAWINGS

An exemplary embodiment of the invention, to which the invention is not restricted however, is schematically represented in the drawing and serves for further explanation of the invention.

DESCRIPTION OF THE PREFERRED EMBODIMENT

In the exemplary embodiment represented there is a production arrangement 1, in particular a hot-rolling mill for producing a product 2, in the present case rolled steel. Not shown in the drawing are the production steps upstream of the hot-rolling mill, that is what is known as the secondary-metallurgical ladle treatment and a casting process, in which the content of a casting ladle is poured, cooled and passed through a tunnel furnace to produce a strip material. All the stages of the production process are provided with a large number of measuring transducers 3, which use measuring lines 4 to pass on measured values, which are used according to the prior art in a production control system for controlling the production arrangement 1 or the upstream production processes. According to the present invention, these measured values ate additionally fed to a first data processing unit, in which a preevaluation or selection is performed, known as aggregation of the data. As indicated in the drawing by an arrow, after hot rolling and annealing, the product 2 runs through under a surface inspection system 6, before it is wound up. The surface inspection system 6 comprises in particular a number of cameras distributed over the width of the product 2, with a downstream, networked image analysis system. Such a system is described for example in the brochure "Automatic Hotstrip Surface Inspection HTS-2W" of Parsytec Computer GmbH, Auf der Huels 183, D-52068 Aachen, Germany. The image data recorded by the cameras can be used to create a kind of surface map of the inspected product, in which specific surface features, in particular defects in the product, are entered, it being possible for different surface features to be classified according to their type, and/or their shape and/or their size and/or their frequency and/or according to other aspects, whereby the mass of data produced by the cameras is reduced, and evaluated for characterizing the quality of the product. According to the prior art, these quality data can be included with the product produced, for example a roll of steel strip, as a quality certificate. Although the viewing of such surface maps has of course also been able already in the past to provide a person skilled in the art with important information on possible defects or wrongly set parameters in the production process, for example the periodicity of specific surface defects could indicate damage on a roller, it has not been possible in the past for prepared surface data to be used systematically for improved control of the production process.

According to the present invention, the surface data are then fed to a second data processing unit 8, in which aggregation of the data is carried out. Depending on the requirements for this aggregation, the second data processing unit 8 may also be integrated into the image analysis system 7, present in any case, of the surface inspection system 6.

The first data processing unit 5 and the second data processing unit 8 are in connection with a third data processing unit 11 via a first data line 9 and a second data line 10, respectively. In said third data processing unit, the aggregated production data and product data are brought together and investigated in a correlation module 12 for correlations existing between them. Once the amounts of data have been reduced in the upstream data processing units 5, 8 with regard to the correlations respectively to be sought, it is possible in principle to use any known kind of correlation search in the correlation module 12. Various ways of doing; this are known in the literature, it also being possible to use different methods of finding correlations one after the other or at the same time. What are known as "data mining tools" have proven to be particularly favorable for the case described here. Such correlation modules were only used in the past for the finding of correlations between simple product data and the parameters of a production process.

By classification of surface features and preevaluation, the invention makes it possible for the first time to provide surface data in such a way that a correlation with production data is possible. With suitable preselection, the correlation analysis in the correlation module 12 is even quick enough for first results from the beginning of the steel strip to be available already while the same melt is being poured from a casting ladle. Feedback of the result of the correlation into the production process is therefore possible virtually online. In any event, however, it is possible to obtain findings about the relationship between surface data, which in the case of sheet-like products contain the most important information on quality, and production parameters, which until now could not be obtained at all, or only by very long-term observations.

The result is that the present invention produces through an output/display unit 13 specific rules which make it possible to predict specific surface features of the product in the case of specific values for process parameters, and consequently to carry out selective process control to achieve a specific surface quality. What is more, on the basis of the relationships found, measured results of the surface inspection system can be fed directly via a feedback 14 into the production arrangement 1 for the control of process parameters.

The invention makes it possible for findings as to the way in which production parameters interrelate with specific surface properties to be gathered quickly, in particular in the case of a cast-rolling installation for steel sheet, whereby more selective process control is made possible for the production of specific qualities and quicker running in of new installations is made possible. The principle described here on the basis of an example of a rolling mill can also be used with the same advantages in the case of other production installations for flat strip materials, for example coating installations, paper production equipment etc.

LIST OF DESIGNATIONS

1 production arrangement
2 product
3 measuring transducers
4 measuring lines
5 first data processing unit
6 surface inspection system
7 image analysis system
8 second data processing unit
9 first data line
10 second data line
11 third data processing unit
12 correlation module
13 output/display unit
14 feedback

We claim:

1. A method for setting process parameters of a production process for an elongate sheet-like product to achieve a predeterminable quality, with the following features;

recording a plurality of process parameters of the production process as a function of time in the form of process data, processing the process data in at least a first data processing unit and outputting as production data, observing the surface of the product by means of a surface inspection system within or at the end of the production process in a process step, the observation data being used in at least a second data processing unit to record the entire surface as a surface map with established surface features in the form of surface data and to classify the surface features according to various types and/or according to size and/or according to frequency and enter them in the surface map according to their position, outputting the various classes and positions of surface features as product data, feeding the production data and the product data together to at least a third data processing unit and investigating the production data and the product data there for correlations existing between them, with rules as to how the product data depend on specific production data being established, setting the process parameters in accordance with the established rules to achieve a desired quality as a feedback to the production process.

2. The method as claimed in claim 1, the product being rolled steel and the production process being a rolling process, in particular a hot-rolling process in a cast-rolling installation.

3. The method as claimed in claim 1, the surface inspection system being an arrangement having a plurality of sensors, in particular cameras, with downstream image analysis systems.

4. The method as claimed in claim 1, the investigation for correlations between production data and product data being in particular a correlation program, which considers the entropy in the data space and detects correlations by finding data constellations with minimal entropy.

5. The method as claimed in claim 1, the surface inspection system analyzing the surface data online or offline, so that the product data are already available during production and detected correlations can be used directly for setting production parameters to achieve or maintain a predeterminable quality.

6. The method as claimed in claim 1, in which, after detection of certain correlations in the first or second data processing unit, production data or product data which do not show any correlations are filtered out and excluded from the further processing in the third data processing unit.

7. The method as claimed in claim 1, specific production data or product data being paused on in the first data processing unit or second data processing unit without prior analysis, filtering or processing to the third data processing unit, to allow possible correlations with these unprocessed data to be found.

8. A device for setting process parameters of a production process in a production arrangement for an elongate sheet-like product to achieve a predeterminable quality, with the following features:

in the production arrangement there are a plurality of measuring transducers for process parameters of the production process, which are connected to at least a first data processing unit, in which the process data are processed and output as production data, at least one surface inspection system in a stage of the production arrangement, which monitors the surface of the product and is connected to at least a second data processing unit, in which the surface is recorded as a surface map with established surface features in the form of surface data and the surface features are classified according to various types and/or according to size and/or according to frequency and are entered in the surface map according to their position, the various classes and positions of surface features being output as product data, the outputs of the first date processing unit and the second data processing unit are in connection with at least a third data processing unit with a correlation module, so that the production data and the product data can be investigated together for correlations existing between them, it being possible to establish rules as to how the product data depend on certain production data, an output or visual display unit, from which the established correlations and/or rules can be output, so that the production parameters can be set in accordance with the desired product quality as a feedback to the production process.

9. The device as claimed in claim 8, wherein the production arrangement is a strip production arrangement, in particular a cast-rolling arrangement for steel strip.

10. The device as claimed in claim 8, wherein the surface inspection system is an arrangement having a plurality of sensors, in particular cameras, with a downstream image analysis system.

11. The device as claimed in claim 8, wherein the correlation module contains for the investigation of correlations between production data and product data a correlation program which considers the entropy in the data space and detects correlations by finding data constellations with minimal entropy.

12. The device as claimed in claim 8, wherein the output of the third data processing unit is connected to closed-loop and open-loop control devices for the production process, to make possible an automatic or semiautomatic feedback and conversion of the correlation results into the production process.

13. The device as claimed in claim 8, wherein the first, second and third data processing units are arranged spatially apart from one another.

14. The device as claimed in claim 8, wherein the first, second and third data processing units are integrated into a common data processing center.

* * * * *